United States Patent
Simionescu et al.

(10) Patent No.: US 9,283,301 B1
(45) Date of Patent: Mar. 15, 2016

(54) SHAPE-MEMORY SPONGE HYDROGEL BIOMATERIAL

(71) Applicant: Clemson University, Clemson, SC (US)

(72) Inventors: Dan Simionescu, Pendleton, SC (US); Jeremy J. Mercuri, Easley, SC (US)

(73) Assignee: Clemson University, Clemson, SC (US)

( * ) Notice: Subject to any disclaimer, the term of this patent is extended or adjusted under 35 U.S.C. 154(b) by 297 days.

(21) Appl. No.: 13/713,685

(22) Filed: Dec. 13, 2012

Related U.S. Application Data (60) Provisional application No. 61/570,374, filed on Dec. 14, 2011.

(51) Int. Cl.
   *A61L 27/24*   (2006.01)
   *A61F 2/02*    (2006.01)
   *A61F 2/44*    (2006.01)

(52) U.S. Cl.
   CPC . *A61L 27/24* (2013.01); *A61F 2/02* (2013.01); *A61F 2/441* (2013.01)

(58) Field of Classification Search
   CPC ......... A61F 2/4611; A61F 2/442; A61F 2/44; A61F 2002/30563; A61F 2/441
   See application file for complete search history.

(56) References Cited

U.S. PATENT DOCUMENTS

| | | | |
|---|---|---|---|
| 5,773,577 A * | 6/1998 | Cappello | 530/350 |
| 2003/0118692 A1* | 6/2003 | Wang et al. | 426/6 |
| 2006/0002980 A1* | 1/2006 | Ringeisen et al. | 424/426 |
| 2007/0254005 A1* | 11/2007 | Pathak et al. | 424/423 |
| 2007/0270950 A1* | 11/2007 | Trieu | 623/17.11 |
| 2009/0254104 A1* | 10/2009 | Murray | 606/151 |
| 2010/0285094 A1* | 11/2010 | Gupta | 424/429 |

OTHER PUBLICATIONS

Barbosa et al., "Improved and simple micro assay for sulfated glycosaminoglycans quantification in biological extracts and its use in skin and muscle tissue studies", Glycobiology 2003 13(9):647-53.

Berlemann et al., "An injectable nucleus replacement as an adjunct to microdiscectomy: 2 year follow-up in a pilot clinical study", Eur Spine J 2009, 18(11): 1706-12.

Betre et al., "Chondrocytic differentiation of human adipose-derived adult stem cells in elastin-like polypeptide" Biomaterials 2006;27(1):91-9.

Boyd et al., "Injectable biomaterials and vertebral endplate treatment for repair and regeneration of the intervertebral disc" Eur Spine .T 2006;15 Suppl 3:S414-21.

Brown et al., "Evaluation of polymer scaffolds to be used in a composite injectable system for intervertebral disc tissue engineering", J Biomed Mater Res 2005, 74A:32-39.

(Continued)

*Primary Examiner* — Jerry Cumberledge
(74) *Attorney, Agent, or Firm* — Dority & Manning, P.A.

(57) ABSTRACT

A hydrogel biomaterial that can be utilized as a nucleus pulposus replacement material is described. The hydrogel biomaterial can is an elastin-glycosaminoglycan-collagen composite hydrogel biomaterial that can mimic the biochemical and functional characteristics of the human nucleus pulposus. Methods for forming the hydrogel biomaterial are also described as are methods for use of the hydrogel biomaterial, one of which is as an in vivo nucleus pulposus replacement material, another of which is a scaffolding material for use in nucleus pulposus tissue engineering applications.

10 Claims, 7 Drawing Sheets

(56) References Cited

OTHER PUBLICATIONS

Cloyd et al., "Material properties in unconfined compression of human nucleus pulposus, injectable hyaluronic add-based hydrogels and tissue engineering scaffolds", Eur Spine J 2007;16(11): 1892-8.
Goupille et al., "Matrix metalloproteinases: the clue to intervertebral disc degeneration?" Spine 1998, 23(14):1612-26.
Kafienalt et al., "Cleavage of native type I collagen by human neutrophil elastase" Biochem J 1998; 330:897-902.
Kanel et al., "Tissue engineering and the intervertebral disc: the challenges", Eur Spine J 2008 17:S480-91.
Kielty et al., "Elastic fibres", J Cell Sci 2002; 115:2817-28.
Le Maitre et al., "Localization of degradative enzymes and their inhibitors in the degenerate human intervertebral intervertebral disc", J Pathol 2004, 204(1):47-54.
Moss et al., "A Novel Thiol-Modified-Hyaluronan and Elastin-Like Polypetide Composite Material for Tissue Engineering of the Nucleus Pulposus of the Intervertebral Disc.", Spine 2011.
Mow VCaH, W.C. "Basic Orthopaedic Biomechanics" Philadelphia: Lippincott-Raven; 1997.
Narayanan et al. "The specificity of purified porcine pancreatic elastase", Biochem J 1969;114(1):11-7.
O'Halloran et al., "Tissue-engineering approach to regenerating the intervertebral disc", Tissue Eng 2007, 13(8):1927-54.
Roberts et al., "Matrix metalloproteinases and aggrecanase: their role in disorders of the human intervertebral disc." Spine 2000, 25(23):3005-13.
Roughley PJ, "Biology of intervertebral disc aging and degeneration: involvement of the extracellular matrix", Spine 2004, 29(23):2691-9.
Rutges et al., "Increased MMP-2 activity during intervertebral disc degeneration is correlated to MMP-14 levels", J Pathol 2008, 214(4):523-30.
Sekiya et al., "In vitro cartilage formation by human adult stem cells from bone marrow stroma defines the sequence of cellular and molecular events during chondrogenesis", Proc Natl Acad Sci U S A 2002, 99(7):4397-402.
Tu et al., "Glycosaminoglycan—mediated coacervation of tropoelastin abolishes the critical concentration, accelerates coacervate formation, and facilitates spherule fusion; implications for tropoelastin microassembly" Biomacromolecules 2008, 9(7): 1739-44.
Wu et al., "Glycosaminoglycans mediate the coacervation of human tropoelastin through dominant charge interactions involving lysine side chains", J Biol Chem 1999, 274(31):21719-24.
Yu J. "Elastic tissues of the intervertebral disc", Biochem Soc Trans 2002, 3016):848-52.

\* cited by examiner

SHAPE-MEMORY SPONGE HYDROGEL BIOMATERIAL

CROSS REFERENCE TO RELATED APPLICATION

This application claims filing benefit of U.S. Provisional Patent Application Ser. No. 61/570,374 having a filing date of Dec. 14, 2011, the contents of which is incorporated herein for all purposes.

FEDERALLY SPONSORED RESEARCH AND DEVELOPMENT

This invention was made with government support under NIH grant #HL093399. The government has certain rights in the invention, 37 CFR 401.14(f)(4).

BACKGROUND

The intervertebral disc resides between the vertebral bodies of the spine and provides support for spinal load as well as allowing for relative motion between adjacent vertebral bodies. Degeneration of the intervertebral disc is a multi-factor process that leads to pain and temporary or even permanent disability. The economic consequence of intervertebral degeneration has been estimated at $7.6 billion for a single year in the United States alone.

Figure 1:
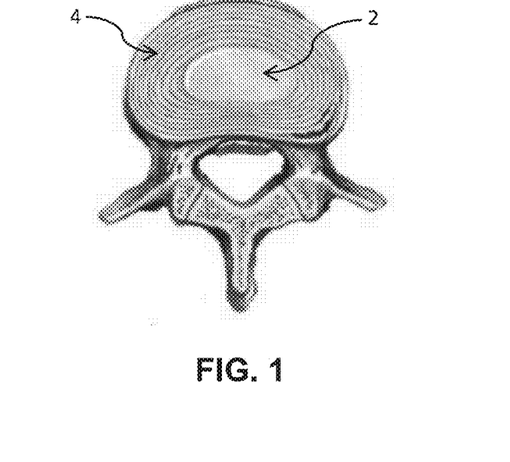
FIG. 1 is a schematic illustrates of an intervertebral disc.

The intervertebral disc includes two distinct regions (FIG. 1) including the nucleus pulposus 2 and the annulus fibrosus 4. Intervertebral disc degeneration is generally initiated within the nucleus pulposus 2, which is formed of a resilient and hydrophilic hydrogel, comprised primarily of collagen type II fibrils randomly oriented within a glycosaminoglycan matrix. Elastin molecules have also been shown to be present in the human nucleus pulposus, and are believed to play a role in aiding the restoration of intervertebral disc matrix deformation. The annulus fibrosus 4 is formed of reinforcing sheets of type I collagen surrounding the nucleus pulposus 2.

Depending upon the nature and severity of the degeneration, treatment options can range from physical therapy or chiropractic treatment, often in conjunction with anti-inflammatory medications, to spinal fusion, in which the intervertebral disc can be completely removed, with many additional options of various severities between the two. Recently, treatment options have been extended to include nucleus pulposus replacement, which can be an option for early stage intervention to remove the source of the degeneration and associated pain without the necessity of spinal fusion.

One difficulty with advancing nucleus pulposus replacement as a viable treatment option has been finding a mimetic surrogate material that can meet both surgical and implant requirements. For instance, the ideal material would be one that could be implanted according to a process that is not overly invasive, e.g., by injection or other minimally invasive procedure. In addition, the ideal material would be tailorable to individual patient anatomy and could provide the necessary mechanical properties while supporting ingrowth of natural tissue so as to regenerate healthy host tissue.

Progress has been made toward developing possible nucleus pulposus replacement materials. For instance, investigators have shown that biomaterials made of soluble elastin-like peptide sequences can promote the differentiation of adult stem cells into a phenotype similar to that of a nucleus pulposus cell, without the use of exogenous supplements and in a low oxygen environment reminiscent of the nucleus pulposus. Injectable biomaterials comprised of elastin have also been developed. Another group has developed and evaluated a chemically modified hyaluronan-elastin-like peptide composite hydrogel for use as a scaffold for nucleus pulposus tissue engineering. Results include improved mechanical properties compared to previous materials, such as gels composed of hyaluronan alone, as well as improved maintenance of human nucleus pulposus cell viability and phenotype over a culture period (e.g., three weeks). In another study, a recombinant protein copolymer of silk and elastin produced by genetically modified $E.\ coli$ bacteria, known as the NuCore Injectable Nucleus (SpineWave, Inc.), has shown promise for use as a cell delivery vehicle. Other studies have illustrated the benefit of glycosaminoglycan-based hydrogels when utilized as nucleus pulposus scaffolds with respect to the maintenance of nucleus pulposus cell viability and phenotype.

Despite such progress, room for improvement in the development of a nucleus pulposus replacement material exists. For instance, problems still exist with materials developed to date such as the need for invasive delivery procedures, the inability to encourage regeneration of healthy host tissue, weak mechanical properties following implant, incomplete in situ curing for injectable materials, the utilization of toxic crosslinking agents, and the possibility of wear debris generation following implant.

Accordingly, what is needed in the art is a viable candidate for use as nucleus pulposus replacement material as well as for use as a scaffold for nucleus pulposus tissue engineering.

SUMMARY

According to one embodiment, disclosed is a hydrogel biomaterial that includes a soluble elastin, collagen, and at least one glycosaminoglycan. The collagen and the glycosaminoglycan are crosslinked to one another, and the soluble elastin is non-fibrous and in the form of microspheres within the hydrogel biomaterial. The hydrogel biomaterial is a shape-memory material that can expel water under a load and regain its original shape following removal of the load.

In one embodiment, the hydrogel biomaterial can be utilized as a nucleus pulposus replacement material.

Also disclosed is a method for replacing nucleus pulposus material. The method comprising compressing the hydrogel biomaterial, inserting the hydrogel biomaterial into an intervertebral disc, rehydrating the hydrogel biomaterial.

Methods for forming the hydrogel biomaterial are also described. For instance, a method can include combining collagen, soluble elastin, and at least one glycosaminoglycan to form a mixture and then heating the mixture to form a gel. The gel can then be crosslinked with a first and a second crosslinking agent. The first crosslinking agent can form crosslinks between the collagen and the glycosaminoglycan(s) and the second crosslinking agent can stabilize the soluble elastin. The method can also include partially degrading the gel following crosslinking with the first and second crosslinking agents with one or more enzymes that target the at least one glycosaminoglycan.

BRIEF DESCRIPTION OF THE FIGURES

A full and enabling disclosure of the present invention, including the best mode thereof to one skilled in the art, is set forth more particularly in the remainder of the specification, which includes reference to the accompanying figures, in which:

FIG. 7 presents macroscopic images depicting the formation of a hydrogel biomaterial to a desired shape within a silicon mold (FIG. 7A) resulting in a nucleus pulposus-like shape for potential patient-tailored use (FIG. 7B, 7C). FIG. 7D illustrates the hydrogel biomaterial compressed for minimally invasive delivery through a 3 mm diameter catheter prototype prior to injection into a NP defect model (FIG. 7E) and re-establishment of its original shape after injection (FIG. 7F).

FIG. 9 illustrates the results of LIVE/DEAD staining following seeding of human adipose derived stem cells (hADSC) on the hydrogel biomaterials at day 7 (FIG. 9A) and day 14 (FIG. 9B). Representative histological images of hADSC seeded hydrogels stained with hematoyxlin (FIG. 9C) and eosin (FIG. 9D) (cell nuclei=arrows), and Alcian blue (FIG. 9E, FIG. 9F) (cell nuclei=arrows).

DETAILED DESCRIPTION

The following description and other modifications and variations to the present invention may be practiced by those of ordinary skill in the art, without departing from the spirit and scope of the present invention. In addition, it should be understood that aspects of the various embodiments may be interchanged in whole or in part. Furthermore, those of ordinary skill in the art will appreciate that the following description is by way of example only, and is not intended to limit the invention.

The present disclosure is generally directed to a hydrogel biomaterial that can be utilized in one embodiment as a nucleus pulposus replacement material that can mimic the biochemical and functional characteristics of the human nucleus pulposus. More specifically, disclosed is an elastin-glycosaminoglycan-collagen composite hydrogel biomaterial, methods for forming the hydrogel biomaterial, and methods for use of the hydrogel biomaterial, one of which is as an in vivo nucleus pulposus replacement material, another of which is a scaffolding material for use in nucleus pulposus tissue engineering applications.

The hydrogel biomaterial can provide the mechanical properties and structural integrity required of a nucleus pulposus replacement, while allowing for nucleus pulposus cell viability and development and maintenance of the desired phenotype. Moreover the hydrogel biomaterial can deform and expel water upon compression and recover both its original shape and water content once unloaded so as to better approximate the diurnal function of the native nucleus pulposus. For example, the hydrogel biomaterial can have water content of greater than about 85%, greater than about 88%, or greater than about 90%.

The hydrogel biomaterial can function as a shape memory sponge material. Concomitant with loading, water is expelled from the material, but upon load removal the material can regain its original shape and imbibe its original water content. This phenomenon appears reminiscent of the diurnal physiology of the native human nucleus pulposus within the intervertebral disc; which loses water and height when loaded throughout the day, but re-absorbs water and regains height during nightly rest periods when unloaded. Moreover, this property may make possible a minimally invasive delivery route for this material into the nucleus pulposus region of the intervertebral disc as well as the moldability of the biomaterial to individual patient anatomy. Without wishing to be bound to any particular theory, it is believed that these physical characteristics of the hydrogel are due to a combination of the components of the hydrogel, which includes one or more glycosaminoglycans and collagen in a crosslinked matrix in conjunction with soluble elastin incorporated throughout the matrix, and the manner in which the formation is carried out.

Figure 2:
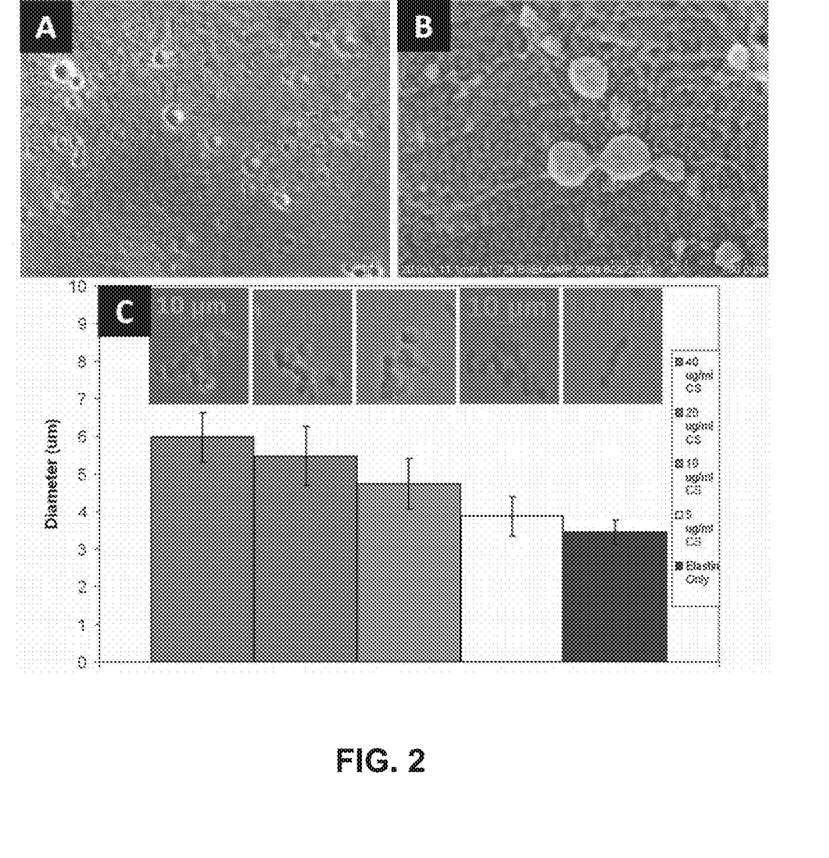
FIG. 2 illustrates a phase contrast (FIG. 2A) and a scanning electron microscopy image (FIG. 2B) of elastin microspheres within a hydrogel biomaterial as described herein. Also shown are images depicting elastin microsphere diameters under phase contrast imaging in conjunction with a graph (FIG. 2C) showing the increase in diameter of microsphere with increasing glycosaminoglycan concentration in the hydrogel biomaterial.

The hydrophilic nature and resistance to compressive loading is believed to be due to the effect of glycosaminoglycan incorporation within the hydrogel biomaterial while resiliency of the material may be at least in part provided by the elastin component. Although the elastin component of the hydrogel biomaterial is soluble and does not form fibers, it has been observed that elastin microspheres tend to coacervate within the hydrogel mixture upon gelation at 37° C., forming spheres that can agglomerate together (FIG. 2A, FIG. 2B). This can also be observed in histological cross-sections of the hydrogels (not shown in FIG. 2). In addition, the diameters of microspheres increase with increasing glycosaminoglycan concentration (FIG. 2O). It is believed that the elastin spheres within the hydrogel biomaterial are stabilized by fixation and can increase resistance of the biomaterial to compressive loads as well as aid in the restoration of the shape following compression.

Although the equilibrium modulus of the material is comparable to values reported for human nucleus pulposus in literature, the material behaves predominantly like an elastic solid. For instance, the equilibrium modulus of the hydrogel biomaterial can be from about 3 kilopascals (KPa) to about 10 KPa or from about 4 kPa to about 6 kPa, for instance 4.73±1.05 kPa. Hysteresis data indicate that a very low percentage of energy is dissipated by the material (about 5 kPa or less, for instance from about 1 kPa to about 3.5 kPa, about 2.24±1.11 kPa). Thus, it is believed that the energy can be stored and released once the load is removed; confirming the relative elasticity of the hydrogel biomaterial.

This is different from the primary load support mechanism of the native nucleus pulposus that largely relies on fluid pressurization due to decreased permeability of the tissue. The hydrogel biomaterial can relax quickly during stress relaxation, potentially due to the porosity of the material and resulting water loss. Overall, the material is very resilient which may be advantageous for maintaining contact with internal surfaces of the intervertebral disc and limiting the potential for device migration and degradation. Furthermore, the release and re-absorption of water from the hydrogel biomaterial upon mechanical perturbation may be beneficial for waste and nutrient transport for cell-seeded constructs for nucleus pulposus tissue regeneration.

The mass loss profile for the hydrogel biomaterial following association with various enzymes indicates that chemical crosslinking is not only necessary for hydrogel formation, but also allows for resistance to enzymatic digestion. For instance, the hydrogel biomaterial can exhibit about a 10% mass loss or less, about a 20% mass loss or less, about a 40% mass loss or less, or about a 60% mass loss or less following association for seven days with one or more enzymes at an enzyme concentration of from about 1 U/ml to about 6 U/ml.

Some variation in mass loss can occur depending upon the specific enzymes associated with the hydrogel biomaterial. This variation in mass loss is likely the result of the relative contributions of each component to the overall hydrogel mass, molecular architecture, the physical interactions of the components, and their respective stabilization with the specific chemical crosslinkers. For example, the greatest amount of mass loss observed in the example section (described in more detail below) was following subjection of the hydrogel biomaterial to elastase digestion. As the soluble elastin component can comprise a large amount of the hydrogel biomaterial (for instance over 53% of the dry mass of the hydrogel biomaterial, in one embodiment), its digestion can result in larger mass loss as compared to other enzymes. Moreover, because the elastin is physically dispersed within the matrix and surrounding both the glycosaminoglycan and collagen components, it is believed that a portion of these elements can be lost during elastin digestion as well. Elastases have been shown to exhibit an affinity for cleaving peptide bonds on the carboxy side of neutral amino acids such as glycine, alanine, and valine, and appear to have an affinity for a broad spectrum of substrates including collagen and proteoglycan. Therefore this broad specificity might also account of the observed mass loss from the hydrogels during digestion by elastases. In comparison, mass loss due to glycosaminoglycan degradation can be minimal (for instance less than about 10% mass loss, less than about 7% mass loss, or less than about 5% mass loss following 7 days of contact with a solution including about 5 U/ml glycosaminoglycan specific enzymes), which can be comparable to values obtained from non-digested biomaterial thus indicates only slight dissolution of the hydrogels due to glycosaminoglycan specific enzymes.

The enzyme degradation profile of the hydrogel biomaterial may be highly advantageous as the degradability of the elastin and collagen components may allow for cellular remodeling of the hydrogel biomaterial over time, e.g., following implant. In addition, the high resistance to glycosaminoglycan degradation can be of great benefit when implanting into degenerative discs, which have been noted to contain increased amounts of glycosaminoglycan degrading enzymes.

During use, the hydrogel biomaterial can exhibit low cytotoxicity, good infiltration of implanted cells, and excellent remodeling capabilities over time. For instance, following initial loading of cells on the hydrogel biomaterial and/or following implant in a cell-rich environment, the cells can infiltrate the hydrogel with little loss in viability overtime. In one embodiment, the hydrogel biomaterial can be loaded with stem cells that can differentiate over time toward a nucleus pulposus cell-like phenotype, which can be utilized in an in vivo application to encourage regeneration of healthy host tissue following implant. Alternatively, the cell compatibility features of the hydrogel biomaterial can be beneficial in an ex vivo or in vitro application, in which the hydrogel biomaterial can function as a cell scaffolding material for growth and development of cells on/in the material.

To form the hydrogel biomaterial, the components of the material including one or more glycosaminoglycans, one or more collagens, and soluble elastin, are combined together to form a mixture. Glycosaminoglycans are long unbranched polysaccharides consisting of a repeating disaccharide unit. The repeating unit (except for keratan) consists of an amino sugar (N-acetylglucose amine or N-acetylgalactose amine) along with a uronic sugar (glucuronic acid or iduronic acid) or galactose. In general, any glycosaminoglycan or combination thereof can be included in the hydrogel biomaterial. A non-limiting list of possibly glycosaminoglycans for inclusion in the material can include chondroitin sulfate, hyaluron (hyaluronic acid), dermatan sulfate, keratin sulfate, heparin, heparin sulfate, and so forth as well as mixtures thereof.

In general, the mixture can include from about 30 wt % to about 50 wt. of the glycosaminoglycan component, for instance between about 35 wt. % and about 45 wt. %, or about 43 wt. % in one embodiment. For example, the mixture can include from about 5 wt. % to about 10 wt. % of a first glycosaminoglycan, e.g., hyaluronic acid, and from about 20 wt. % to about 45 wt. % of a second glycosaminoglycan, e.g., chondroitin sulfate. Of course, the mixture can include more than two glycosaminoglycans in any suitable proportion to one another.

The mixture also include from about 2 wt. % to about 10 wt. % or from about 3 wt % to about 7 wt. %, for instance about 4 wt. % of a solubilized collagen. Collagens are insoluble, extracellular glycoproteins that are found in all animals and are the most abundant proteins in the human body. To date, 19 types of collagens have been found in humans. The major types include Type I, which is the chief component of tendons, ligaments, and bones; Type II, which represents more than 50% of the protein in cartilage, and is also used to build the notochord of vertebrate embryos; Type III, which strengthens the walls of hollow structures like arteries, the intestine, and the uterus, and Type IV, which forms the basal lamina of epithelia. A meshwork of Type IV collagens provides the filter for the blood capillaries and the glomeruli of the kidneys. The other 15 types of collagen, while being much less abundant, are no less important. The basic unit of collagens is a polypeptide that often follows the pattern Gly-Pro-Y or Gly-X-Hyp, where X and Y may be any of various other amino acid residues. The resulting polypeptide is twisted into an elongated, left-handed helix. When synthesized, the N-terminal and C-terminal of the polypeptide have globular domains, which keep the molecule soluble. In one embodiment, the mixture can include solubilized type I collagen, though this is not a requirement of the material, and other types of collagens as well as mixtures of collagens can be included in the mixture.

The mixture also includes a soluble elastin component. Elastin is the protein constituent of connective tissue responsible for the elasticity and recoil of the tissue and is quite abundant in connective tissue. Soluble tropoelastin chains are naturally cross-linked together to form elastic fibers. In the mixture, soluble elastin is utilized, which can be either natural tropoelastin materials that have not been crosslinked or alternatively can be solubilized elastin that is formed from cross-linked elastin fibers. For example, soluble elastin can be formed according to the method of Partridge, et al. (Biochem, J., 61, 11 (1955)). According to this process, bovine neck ligament elastin is solublized with hot oxalic acid solution, clarified, diaylzed and lyophilized. Of course, any other suitable source of soluble elastin can alternatively be utilized. The mixture can generally include from about 40 wt. % to about 70 wt. % of the soluble elastin component, for instance from about 45 wt. % to about 65 wt. % or from about 50 wt % to about 60 wt. %.

The mixture can include one or more other components as are generally known in the art for incorporation into the hydrogel biomaterial. For example, the mixture can include biologically active agents that can encourage growth and development of cells within the hydrogel biomaterial or within the implant area of the hydrogel biomaterial. The mixture can include materials for delivery to the local area to prevent rejection and/or infection. By way of example, and without limitation, the mixture can include one or more antibiotics, antimycotics, enzyme inhibitors, anti-inflammatory drugs and/or other drugs as are generally known in the art.

The components are combined at relatively low temperature, for instance less than about 20° C., or less than about 10° C., and then heated to gel the matrix. For instance the mixture can be heated to a temperature of from about 30° C. to about 40° C., for instance about 37° C. for a period of time (e.g., about two hours) to form a gel.

To chemically crosslink the gel, the gel can be lyophilized and chemically crosslinked with a combination of a first crosslinking process that can primarily form crosslinks between the collagen component and the glycosaminoglycan component of the hydrogel biomaterial and a second crosslinking process that can stabilize the elastin component of the hydrogel biomaterial. It should be noted that though discussed herein as a first and second crosslinking process, this terminology is not intended to limit the order of the two processes in any fashion. In particular, the two processes can be carried out in any order or simultaneously.

The first crosslinking process can incorporate one or more crosslinking agents capable of forming chemical crosslinks at carboxylic acid groups so as to form chemical bonds between the collagen component and the glycosaminoglycan component of the hydrogel biomaterial. Such crosslinking agents are well known in the art, any of which may be utilized in forming the hydrogel biomaterial. For instance carbonyldiimidazole (CDI) can be used in non-aqueous conditions to activate carboxylic acids for direct conjugation to primary amines (—$NH_2$) via amide bonds.

In one embodiment, the carboxylic acid crosslinking agent can utilize carbodiimide chemistry in forming crosslinks in the gel. Carbodiimide compounds provide a relatively versatile method for crosslinking at carboxylic acids. The most readily available and commonly used carbodiimides are the water-soluble ethyl-3-(-3-dimethylaminopropyl) carbodiimide hydrochloride (EDC) for aqueous crosslinking and the water-insoluble N',N'-dicyclohexyl carbodiimide (DCC) for non-aqueous methods. They cause direct conjugation of carboxylates (—COOH) to primary amines (—$NH_2$) without becoming part of the final crosslink (amide bond) between target molecules.

An EDC crosslinking process can generally be carried out in conditions devoid of extraneous carboxyls and amines. For example, use of acidic (pH 4.5 to 5.5) 4-morpholino-ethanesulfonic acid (MES) buffer can be utilized or phosphate buffers at pH of less than about 7.2, which are also compatible with the carbodiimide reaction chemistry.

A crosslinking agent for use in the first crosslinking process can generally be provided in a concentration of about 30 mM or greater, about 40 mM or greater, or about 50 mM or greater. For instance, the crosslinking agent for the first crosslinking process can be provided in a concentration of from about 35 mM to about 100 mM, or from about 40 mM to about 90 mM.

N-hydroxysuccinimide (NHS) or its water-soluble analog (Sulfo-NHS) can be included in an EDC crosslinking process to improve efficiency and to create a more stable, amine-reactive intermediate. For instance, NHS can be provided to the first crosslinking process in conjunction with EDC in a concentration of about 6 mM or greater, about 8 mM or greater, or about 10 mM or greater. For example, NHS can be provided in a concentration of from about 6 mM to about 20 mM, or from about 10 mM to about 15 mM.

The second crosslinking process can stabilize the elastin component of the hydrogel biomaterial. More specifically, the second crosslinking process can utilize a phenolic compound that includes multiple phenolic groups bound to a hydrophobic core as a crosslinking agent. The phenolic compound can bind the elastin via hydrogen bond formation with polar amino acid residues such as methionine, glycine and proline. The presence of multiple binding sites on the phenolic compound can provide for multiple elastin molecules to interact with a single phenolic molecule to create a three-dimensional cross-link structure involving multiple elastin molecules. Moreover, and depending upon the specific phenolic compound, covalent bonds can be formed between the phenolic compound and the elastin, in addition to the hydrogen bonding.

Phenolic compounds encompassed herein include materials including a hydrophobic core and multiple phenol groups extending from the hydrophobic portion of the molecule. For instance, exemplary phenolic compounds can include, but are not limited to, flavonoids and their derivatives (e.g., anthocyanins, quercetin), flavolignans, phenolic rhizomes, flavan-3-ols including (+)-catechin and (−)-epicatechin, other tannins and derivatives thereof (such as tannic acid, pentagalloylglucose, nobotanin, epigallocatechin gallate, and gallotannins), ellagic acid, procyanidins, and the like.

Phenolic crosslinking agents include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaimic*, extracts of licorice, sea whip, aloe vera, chamomile, and the like.

Figure 3:
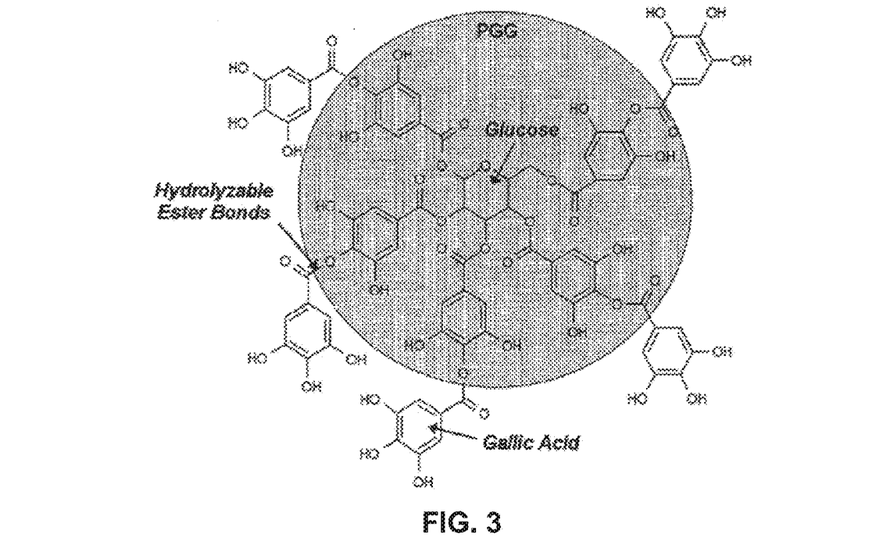
FIG. 3 schematically illustrates the structure of tannic acid.

In one embodiment, the phenolic can be a tannin or a derivative thereof. Tannic acid, the structure of which is illustrated in FIG. 3, is a common naturally derived tannin. At one time, tannic acid-containing preparations were suspected of causing hepatoxicity. This toxicity has since been primarily attributed to poor purity of the preparations and the inclusion of toxic gallic acid residues in the compositions. Thus, when utilized as a crosslinking agent, high purity tannic acid with little or no free gallic acid residue can be used. For example, a tannic acid crosslinking agent can include less than about 5 wt. % free gallic acid residues or between about 1 wt. % and about 5 wt. % free gallic acid residues.

One phenolic crosslinking agent encompassed herein is pentagalloylglucose. Pentagalloylglucose, which is the portion of a tannic acid molecule enclosed in the circle in FIG. 3, includes the hydrophobic core of tannic acid as well as multiple phenolic hydroxy groups, but does not possess the outer gallic acid residues and the hydrolyzable ester bonds associated with tannic acid. Thus, the possibility of release of free gallic acid residues over time can be minimized through utilization of a compound having no gallic acid residues, such as PGG, as the selected crosslinking agent.

The second crosslinking process can be carried out by simply submerging the gel into a solution (e.g., about 2 wt % or less) of the second crosslinking agent for a period of time, generally about 12 hours or more.

Following formation of this highly crosslinked matrix, the highly crosslinked matrix can be partially degraded via a controlled enzymatic degradation. Without wishing to be bound to any particular theory, it is believed that partial enzymatic degradation of the crosslinked matrix increases the water absorption capabilities of the hydrogel biomaterial without severely degrading the physical characteristics of the hydrogel. Thus, the partially degraded hydrogel biomaterial can exhibit excellent physical characteristics and extreme resiliency while still exhibiting high water absorption and shape memory following loss and reabsorption of water.

Figure 4:
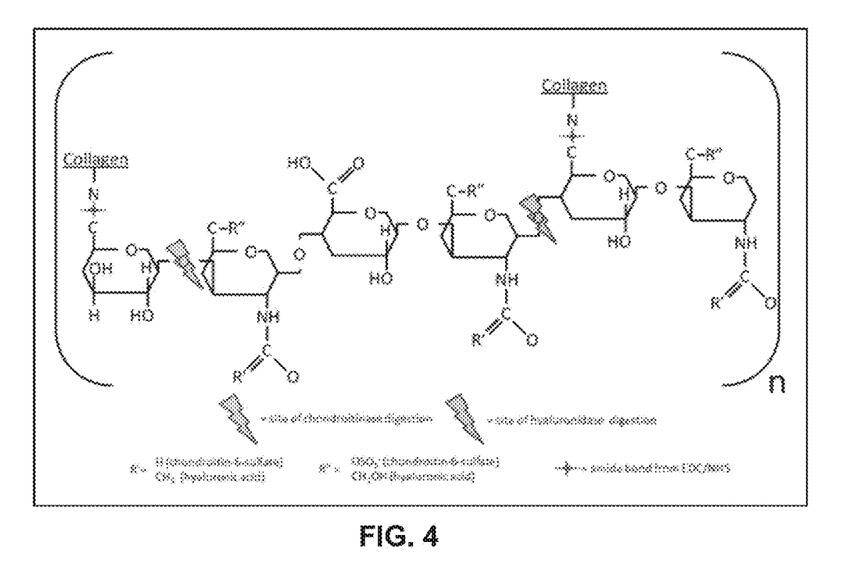
FIG. 4 schematically illustrates the partial degradation of a matrix at glycosaminoglycan sites to form the hydrogel biomaterial.

The partial degradation of the crosslinked matrix is carried out by one or more enzymes that target the glycosaminoglycan component of the crosslinked gel, the specific types of which will depend upon the glycosaminoglycans utilized in forming the gel. The total concentration of the enzymes can generally be less than about 10 U/ml, for instance between about 1 and about 8 U/ml, or between about 2 and about 7 U/nil. FIG. 4 schematically illustrates the partial degradation of a matrix that includes a glycosaminoglycan component formed of a mixture of chondroitin sulfate and hyaluronic acid. The crosslinking of the components of the hydrogel biomaterial results in glycosaminoglycan cross-bridge formation between collagen fibers as shown in FIG. 4 and consequently will yield a relatively stiff and brittle hydrogel. However, following partial enzymatic degradation, it is believed that some of the cross-bridges are broken at the glycosidic bonds (FIG. 4), which can allow for an increase in the deformational properties while still maintaining the hydrophilic nature of the hydrogel biomaterial.

The partial degradation can be carried out by merely soaking the crosslinked gel in a solution of the enzymes for a period of time, generally less than about 24 hours. Following partial degradation, the enzymes can be deactivated, for instance by heat, e.g., about 55° C. for about one hour.

As previously stated, in one application, the hydrogel biomaterial can be used as a nucleus pulposus replacement material. For this application, the biomaterial can be used with or without autologous cells for replacement and ultimately regeneration of the intervertebral disc tissue. Additionally, the material could also serve as a delivery vehicle for growth and differentiation factors including, but not limited to transforming growth factor beta (TGF-β), vascular endothelial growth factor (VEGF), epidermal growth factor (EGF), fibroblast growth factor (FGF), growth differentiation factors (GDF's), insulin-like growth factor (IGF) and cytokines for the for the specific application of nucleus pulposus tissue regeneration or for other regenerative medicine applications.

Due to the shape retention and high water absorbability of the hydrogel biomaterial, deliver of a material to an implant site can be relatively non-invasive. For instance, following removal of nucleus pulposus material from a site, the hydrogel biomaterial can be compressed with water removed and delivered through a catheter to the site, followed by addition of water at the site to return the biomaterial to the hydrated form. Moreover, the characteristics of the hydrogel biomaterial can allow it to be shaped prior to implantation to meet the individual specifications of the implant site, which can further improve long term implant of the biomaterial.

The hydrogel biomaterial is in no way limited to utilization as an implant material, however. In one alternative application, the hydrogel biomaterial can be used to as an adjunct to spinal fusion hardware in which it could be loaded with or without autologous osteoblast cells in conjunction with bone morphogenetic proteins, for instance to promote spinal fusion. In an alternative application, the hydrogel biomaterial can be used as a coating for metallic implantable materials to allow for and promote host cell/tissue integration and regeneration.

In another embodiment, the hydrogel biomaterial can be utilized in cosmetic and reconstructive surgery, for instance for breast augmentation or reconstruction, and as soft tissue fillers for placement in lips, dermis, ears, nose, cheeks, and adipose tissue. The material may find use as a broad-based biomaterial for implantation to replace and or regenerate tissue in addition to cosmetic applications. One example would be its use as a myocardial plug to help regenerate heart tissue after a myocardial infarction. Or as a general three dimensional substrate on which to grow cells in vitro.

The hydrogel biomaterial can also be utilized for promoting articular cartilage regeneration and can be used in conjunction with or without autologous cells. In one particular embodiment, the hydrogel biomaterial may be used as an adjunct to knee cartilage repair using the micro-fracture technique. This material could be placed into the subchondral defect site created during the micro-fracture technique in a partially dehydrated and compressed state allowing the material to absorb the resultant bone marrow, blood, growth factors and progenitor cells that leach from the fracture site thus localizing all of these healing factors at the site of repair. This material could then be secured in place to allow for cartilage regeneration using a periosteal patch and sutures.

The present disclosure may be better understood with reference to the Example, below.

EXAMPLE

Hydrogel Biomaterial Preparation

Hyaluronic acid (5 mg/ml) (Sigma Aldrich), chondroitin-6-sulfate (27 mg/ml) (Sigma Aldrich), and soluble elastin (40 mg/ml) (Elastin Products Company) were combined sequentially with a neutralized solution of soluble type I collagen (3 mg/ml) (PureCol-Advanced BioMatrix) and mixed on ice. The solution was transferred into 2 ml microfuge tubes in 0.5 ml aliquots and subsequently gelled at 37° C. for two hours. The formed gels were then lyophilized and chemically stabilized in the microfuge tubes via the addition of 1.5 ml of 60 mM 1-Ethyl-3-(3-dimethylaminopropyl) carbodiimide EDC/12 mM N-Hydroxysuccinimide (EDC/NHS) for 24 hours. It was determined from preliminary studies that hydrogel crosslinking with lower concentrations of EDC/NHS (15 mM EDC/3 mM NHS and 30 mM EDC/6 mM NHS) did not result in a hydrogel with the desired sponge-like properties (data not shown). Following thorough rinsing in water, hydrogels were submerged in 1.5 ml of 0.15% pentagalloyl glucose (Ajinmoto OmniChem) in PBS (pH 7.4) for 24 hours for further chemical stabilization prior to rinsing in water and enzymatic processing with a mixture of glycosaminoglycan degrading enzymes (0.1 U/ml chondroitinase ABC and 5.0 U/ml hyaluronidase in 100 mM ammonium acetate buffer; pH 7.4) (Sigma Aldrich) for 19 hours. Pilot studies utilizing various concentrations of either collagenase, elastase or a mixture of glycosaminoglycan degrading enzymes indicated that only when the hydrogels were digested with the glycosaminoglycan degrading enzymes was a resilient hydrogel formed. Hydrogel samples were then incubated at 55° C. for 1 hour to inactivate the enzymes followed by thorough rinsing in water.

A literature review confirming enzyme denaturation temperatures and pilot studies confirming enzyme inactivation via an enzyme kinetics study were completed (data not shown). Furthermore, differential scanning calorimetry was performed on the crosslinked hydrogels to determine thermal denaturation temperature of the hydrogels (84.79±3.54° C.) and qualitative mechanical analysis indicated that the hydrogels were not detrimentally altered by the heat treatment (data not shown). For cell culture studies the resulting hydrogels were sterilized via submersion in a solution of 0.1% peracetic acid in phosphate buffered saline (pH 7.4) for four hours, prior to thorough rinsing and incubation in a 50:50 mixture of fetal bovine serum and Dulbecco's Modified Eagle's Medium containing 1% antibiotic/antimycotic.

Biomechanical Characterization

Compressive mechanical properties were evaluated in unconfined conditions under displacement control with samples (n=6) submerged in 37° C. PBS. The testing protocol included the application of a 0.05N pre-load immediately followed by pre-conditioning using ten cycles of compression to 25% strain. The tenth cycle was used to calculate hysteresis and apparent linear region modulus. Additionally, hydrogel wet weights were measured prior to and immediately following testing to determine the change in water content to illustrate the hydrogels capacity to retain and re-absorb water. Next, hydrogels were unloaded and subjected to incremental stress relaxation testing to a final strain of 25% using 5% strain increments held for twenty minutes each. The equilibrium modulus was determined from the slope of an equilibrium stress versus applied strain plot. Additionally, semi-quantitative testing of hydrogel resiliency following unconfined compression was performed using video capture and digital imaging software to track pre- and post-compression hydrogel height and time to recovery.

Hydrogel Biomaterial Molding and Minimally Invasive Delivery

The ability of the hydrogels to be molded into a nucleus pulposus-like shape and subsequently delivered via a minimally invasive cannula as might be performed in surgery was evaluated in a feasibility study. Briefly, a hydrogel was manufactured as previously described; however the hydrogel solution was gelated, lyophilized, and crosslinked within a silicon mold shaped to mimic the anatomic geometry of the human nucleus pulposus. The hydrogel and mold were confined in a histological processing cassette to allow for adequate chemical fixation while maintaining the integrity of the hydrogel during crosslinking. The resultant hydrogel was compressed on a sterile field to remove water while concurrently being rolled into small pellet that was inserted into a plastic pipette tip which served as a catheter surrogate. The hydrogel was then advanced through the pipette tip via water and its ability to return to its original shape was qualitatively evaluated.

Resistance to Enzymatic Degradation

Hydrogel component stabilization and overall resistance to enzymatic degradation was determined by evaluating the change in hydrogel dry mass following digestion in elastin, glycosaminoglycan and collagen degrading enzymes, respectively. Hydrogel samples (n=4 per study group per time point) were incubated in either a solution of 1 U/ml collagenase or 1 Mini elastase (both in 50 mM Tris, 10 mM $CaCl_3$; pH 7.6, or a mixture of glycosaminoglycan degrading enzymes (0.1 U/ml chondroitinase ABC and 5.0 U/ml hyaluronidase in 100 mM ammonium acetate buffer; pH 7.4) at 37° C. for 2 and 7 days. Additionally, non-crosslinked hydrogels digested in each respective enzyme solution and non-digested crosslinked hydrogels served as control groups for comparison. Percent mass loss was determined gravimetrically for each hydrogel by comparing pre- and post digestion sample dry weights.

Adipose Derived Stem Cell Differentiation and Glycosaminoglycan Production on/in Hydrogel Biomaterial Human adipose derived stem cells (hADSC) were expanded in MesenPro Complete stromal growth media (Invitrogen) and cells from passage 2-4 were seeded onto the hydrogels by exploiting the sponge-like characteristic of the material. Briefly, hydrogels pre-incubated in a media (described above) were partially dehydrated via manual compression with sterile forceps on a sterile field. Hydrogels were rehydrated via the drop-wise addition of 200 μl of differentiation media containing approximately 800,000 hADSCs. The cell suspension was absorbed into the material which concomitantly expanded and re-acquired its pre-dehydrated shape resulting in a targeted seeding density of $4 \times 10^5$ cells/$cm^3$. Composition of the differentiation media and the methods regarding gene expression (n=3 samples per time-point), DNA content (n=3 samples per time-point), LIVE/DEAD (n=2 samples per time point), and histological analyses (n=2 per time-point) were performed as described previously. Total sulfated glycosaminoglycan content was quantified using the DMMB assay as described by Farndale et al. with modification. Hydrogel samples (n=3 per time-point) were digested in 15 mg/ml proteinase K (Qiagen) in 30 mM Tris (ph 8.0) for 24 hours. Samples were diluted 25× in 30 mM Tris buffer and a 50 μl aliquot of diluted sample was added to 200 μl of DMMB reagent in triplicate in a 96-well plate. Optical absorbance was read at 525 nm and glycosaminoglycan content was determined via a standard curve developed from serial dilutions of known concentrations of chondroitin sulfate sodium salt. Values were normalized to sample dry weights and compared with non-cell seeded hydrogel controls.

In-Vivo Biocompatibility

Hydrogel biocompatibility was assessed using an in-vivo subcutaneous model in male Sprague-Dawley rats. Hydrogels were prepared sterile as described above prior to lyophilization and storage in sterile 2 ml microfuge tubes until the time of implant. One small incision was made transversely to the dorsal mid-line of each animal in which two subdermal pockets were made. One sterile hydrogel was placed into each pocket, yielding two implants per rat. Incisions were closed with surgical staples. A minimum of 4 rats received two implants yielding at least 8 implants for analysis. Histological and immunohistochemical analysis was performed as outlined in Chapter 4.

Statistics

All results are expressed as a mean±standard deviation. One-way analysis of variance (ANOVA) using Fishers Least Significant Difference post hoc multiple comparison procedures and Student's West of unequal variance was used for statistical analysis when appropriate. Significance was defined in all cases as $p < 0.05$.

Biomechanical Characterization

Figure 5:
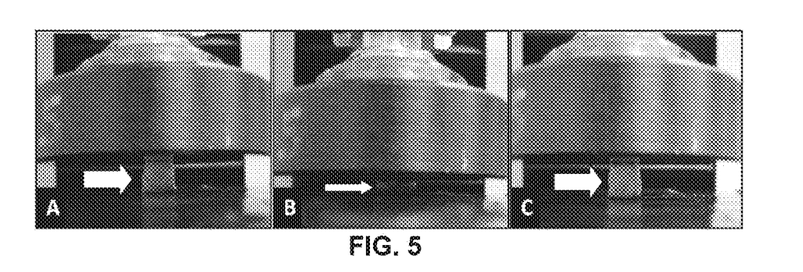
FIG. 5 illustrates representative time-lapse images depicting a hydrogel biomaterial prior to (FIG. 5A), during (FIG. 5B), and immediately following (FIG. 5C) unconfined compressive loading achieving greater than 75% strain.

FIG. 5 illustrates representative time-lapse images depicting a hydrogel biomaterial prior to (FIG. 5A), during (FIG. 5B), and immediately following (FIG. 5C) unconfined compressive loading achieving greater than 75% strain. As can be seen, during the compressive biomechanical testing the hydrogels exhibited the ability to deform while concurrently expelling water. All hydrogels maintained contact with the platen throughout testing illustrating resiliency. As the load was removed, the material returned to its original height and shape while re-absorbing its original water content instantaneously exhibiting a sponge-like characteristic as shown in the table, below. This phenomenon continued to be observed even after multi-cycle unconfined compression testing to applied strains exceeding 50%.

|  | Loading | Loading | (Seconds) |
|---|---|---|---|
| Hydrogel biomaterial height recovery | — | 96.4% ± 1.3% | 2.5 ± 0.2 |
| Hydrogel biomaterial water content | 94.5% ± 0.6% | 89.2% ± 9.4% | |

Figure 6:
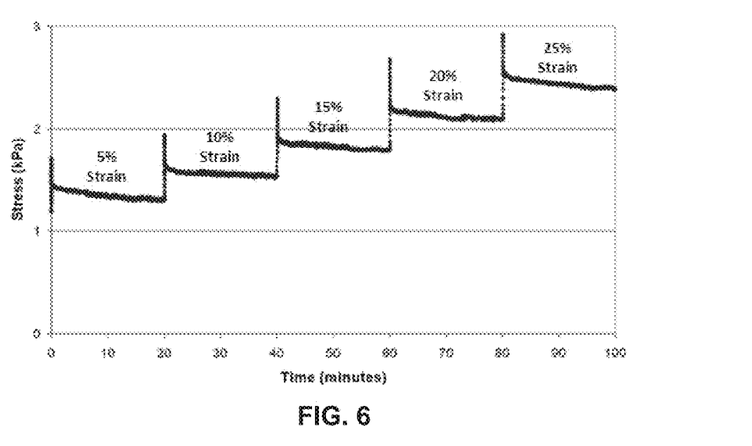
FIG. 6 illustrates the incremental stress relaxation curve for the hydrogel biomaterial, demonstrating the time-dependent viscoelastic nature of the hydrogel.

Multi-cycle hysteresis (data not shown) and incremental stress relaxation testing (FIG. 6) indicated that hydrogel biomaterials behaved as a viscoelastic solid with a predominantly elastic characteristic. The linear region modulus, percent energy dissipation and equilibrium modulus values for the hydrogels were 4.16±1.11 kPa, 2.24±1.34% and 4.73±1.05 kPa, respectively.

Hydrogel Biomaterial Molding and Minimally Invasive Delivery

Figure 7:
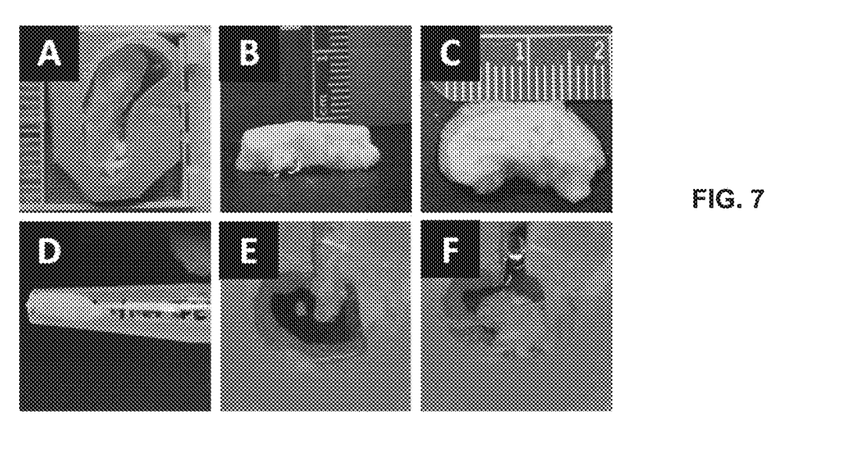

As shown in FIG. 7, the hydrogel biomaterial exhibited the ability to be to molded/formed into a complex shape (FIG. 7A) resembling the geometry of the nucleus pulposus region of the human intervertebral disc with remarkable fidelity. Moreover, the resulting hydrogel with its largest dimension being approximately 20 mm (the height of the shaped material is shown in FIG. 7B and the width is shown in FIG. 7C) exhibited the ability to be compressed and rolled into a pellet with a resultant outer diameter of less than 4 mm (FIG. 7D). The hydrogel was advanced through the end of a catheter surrogate via water (FIG. 7E) and subsequently was able to re-establish its original geometry (FIG. 7F). Some fracture was noted around the hydrogels edges; however the bulk material remained intact.

Resistance to Enzymatic Degradation

Figure 8:
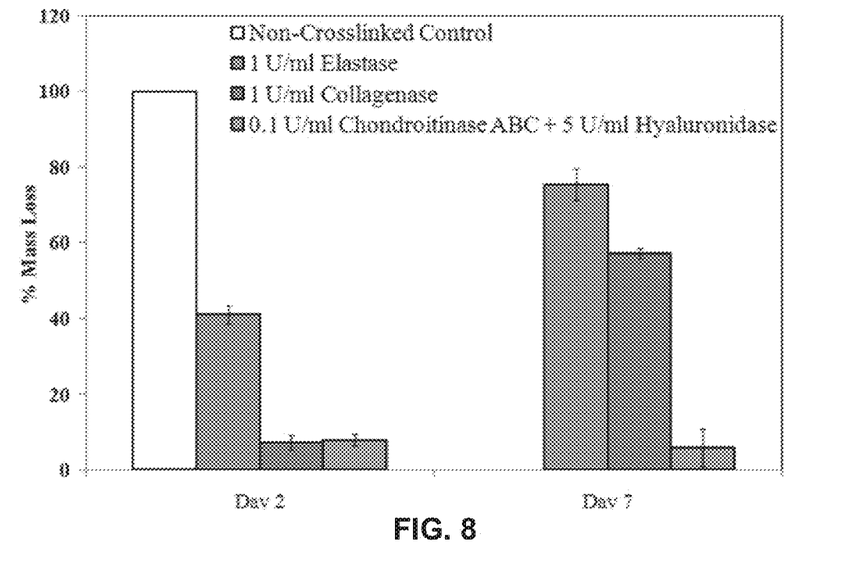
FIG. 8 illustrates the mass loss of a hydrogel biomaterial following two and seven days of digestion in different enzymatic conditions.

The hydrogel biomaterial exhibited the ability to resist accelerated enzymatic digestion which was determined via mass loss measurements following a total of 7 days of enzymatic digestion in collagen, elastin, and glycosaminoglycan degrading enzymes, respectively (FIG. 8). Results indicated that each component of the hydrogel was stabilized to different extents. It was observed that all non-crosslinked enzyme digested controls completely degraded within the first three hours of digestion. Conversely, non-digested crosslinked controls exhibited minimal mass loss (~5%, data not shown) by day 7 indicating negligible scaffold dissolution. Furthermore, two and seven day mass loss results illustrated that the elastin and collagen components of the hydrogel were degradable. Mass loss due to elastin degradation increased from 41.07±2.27% to 75.48±4.14% from day 2 to day 7, while mass loss due to collagen degradation increased from 7.22±1.84% to 57.21±1.44%. The glycosaminoglycan component of the hydrogels appeared the most resistant to enzymatic digestion. Following exposure to a mixture of glycosaminoglycan degrading enzymes, only 6-7% of the hydrogels mass was lost by day 7 of the study.

Figure 9:
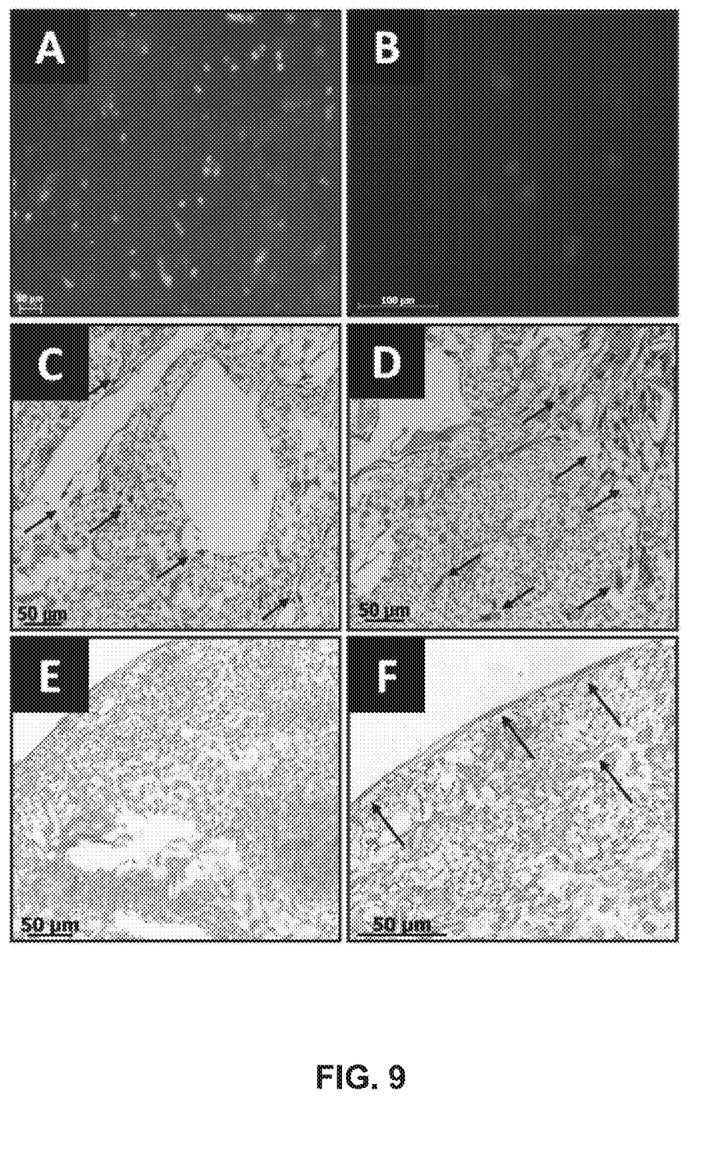

Adipose Derived Stem Cell Differentiation and Glycosaminoglycan Production on/in Hydrogel Biomaterials As shown in FIG. 9A and FIG. 9B, LIVE/DEAD analysis indicated that a majority of the hADSCs remained viable throughout the 14 day culture period as the majority of the cells stained fluorescent green when cultured on the hydrogels. Similar results were also observed following seeding of porcine nucleus pulposus cells on hydrogels and subsequent culture for up to 28 days (data not shown). Hematoxylin (FIG. 9C) and Eosin (FIG. 9D) staining indicated that the hADSCs were found predominantly lining the outer surface of the hydrogels, however some cells were found lining large internal pores and within the matrix of the center of the hydrogel. Alcian blue staining (FIG. 9E, FIG. 9F) confirmed the relative distribution of hADSCs while illustrating the hydrogels porous micro-architecture composed of globular elastin molecules distributed within a glycosaminoglycan-rich matrix.

Figure 10:
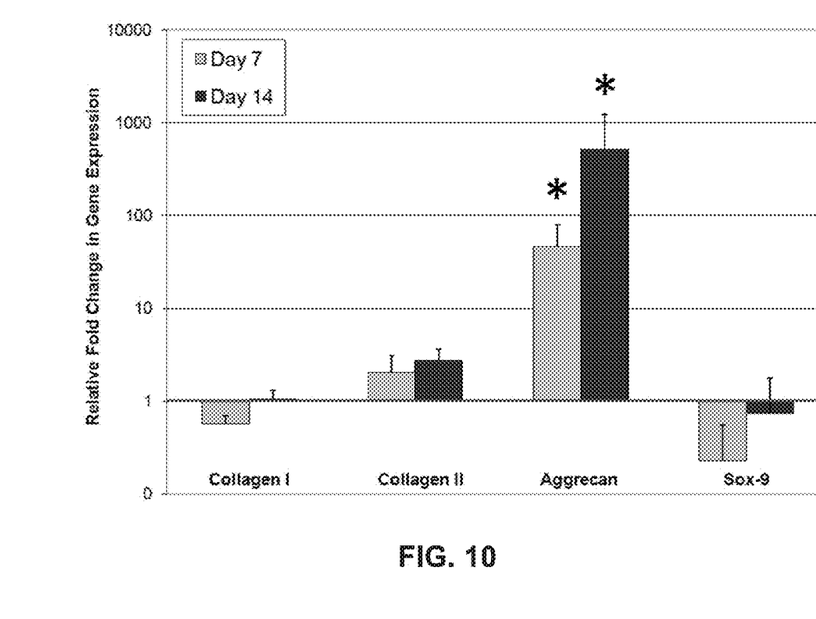
FIG. 10 presents the gene expression profile of hADSCs cultured on the hydrogels in the presence of differentiation media.

Gene expression profiles of hADSCs seeded on the hydrogels cultured in differentiation media were evaluated to determine if nucleus pulposus cell-like gene expression profile could be achieved (as indicated by collagen type II, aggrecan, and Sox-9 gene markers). By day 14 hADSCs cultured in differentiation media exhibited an increased expression for NP cell markers collagen type II (2.75-fold increase) and aggrecan (>100-fold increase) relative to non-differentiated hADSCs (FIG. 10), however there was considerable variability in gene expression noted within the small sample size analyzed. In FIG. 10, data is represented as a relative fold change compared to undifferentiated stem cells, (* indicates statistical difference compared to corresponding time-point in the positive control group (data not shown), $p<0.05$.)

It was noted that minimal collagen type I expression was observed in hADSCs cultured on the hydrogels in the presence of differentiation media. Interestingly sox-9 expression illustrated an increasing trend from day 7 to day 14; however these levels never exceeded the expression of undifferentiated hADSCs.

Figure 11:
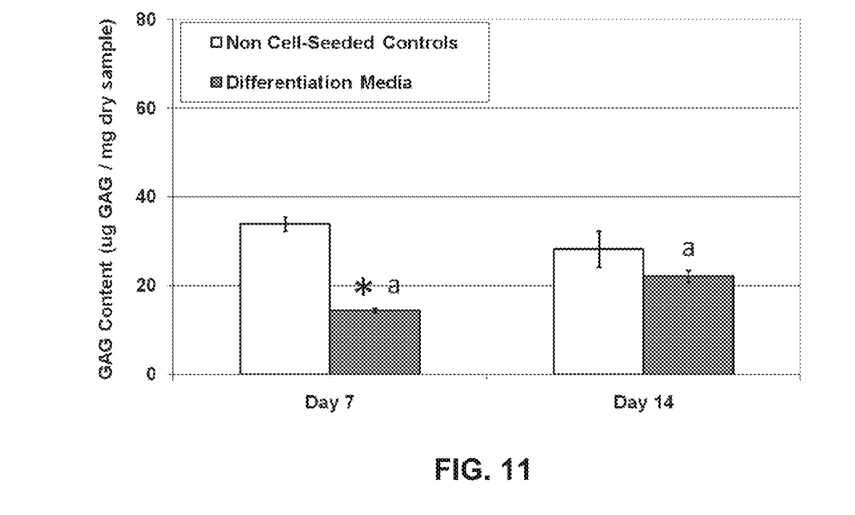
FIG. 11 illustrates glycosaminoglycan content of hADSC seeded the hydrogels normalized to sample dry weight.

Glycosaminoglycan (GAG) content measurements of the hydrogels (FIG. 11) indicated that non cell-seeded controls had significantly more glycosaminoglycan after 7 days of culture compared to hADSC seeded hydrogels (33.94±1.59 and 14.42±0.51 μg GAG/mg dry sample, respectively) ($p<0.05$). However, after 14 days of culture the glycosaminoglycan content of the hADSCs seeded hydrogels significantly ($p<0.05$) increased as compared to hASDC seeded hydrogels at day 7, reaching a value of 22.15±1.28 μg GAG/mg dry sample, which was not significantly different from day 14 non cell-seeded controls. (* Indicates statistical difference compared to non-cell-seeded controls at the corresponding time-point. Letters indicate a significant difference comparing between time-points within the same study group. $p<0.0$)

In-Vivo Biocompatibility

Figure 12:
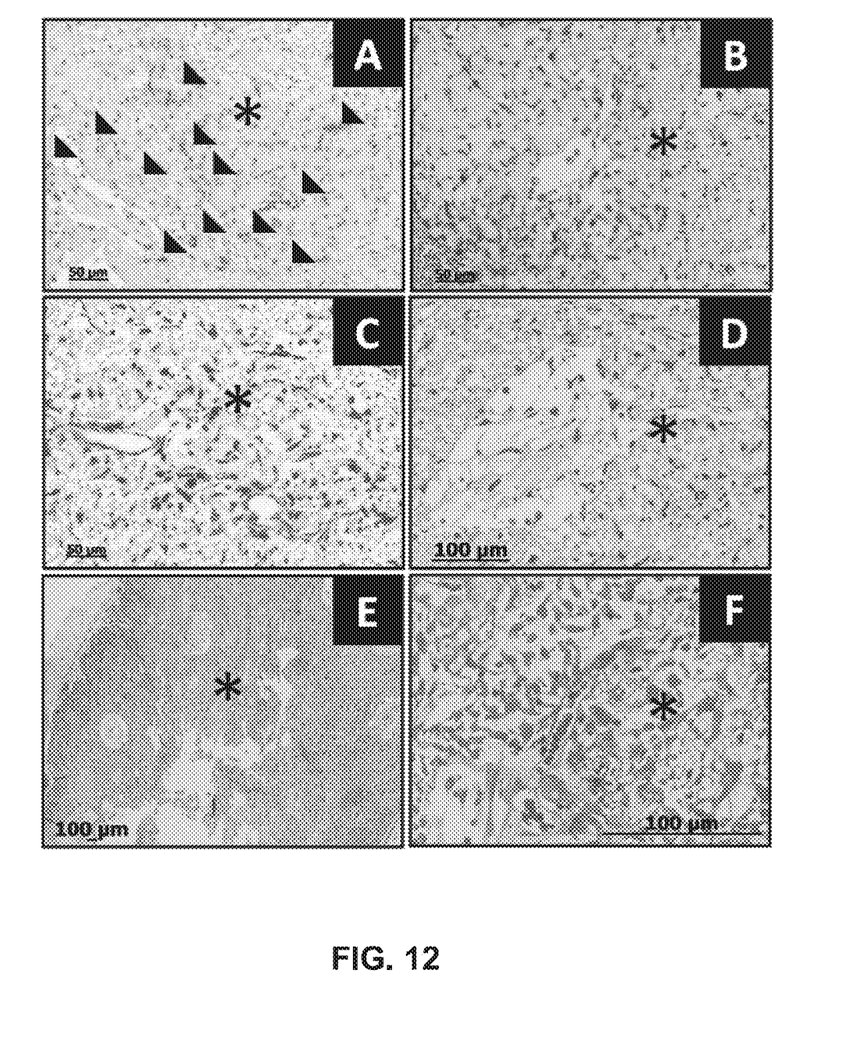
FIG. 12 presents representative histological sections of hydrogels following 4 weeks of subdermal implantation. Immunohistochemical staining for T-cells (arrows) (FIG. 12A), macrophages (FIG. 12B), vimentin/fibroblasts (FIG. 12C), and prolyl 4-hydroxylase (FIG. 12D). Gomori's trichrome staining for collagen is shown in FIG. 12E and FIG. 12F.

Initial gross observation of explanted hydrogels indicated that the overall size of the hydrogels were not noticeably different compared to pre-implantation, however no quantitative mass or dimensional measurements were taken. Upon microscopic observation of explanted hydrogel sections, it appeared that some of the hydrogels exhibited signs of degradation within their interstice (FIG. 12), Moreover, it was apparent that host cells were able to infiltrate the entire depth of the material. Many of the larger pores found within the hydrogels were infiltrated with active fibroblasts producing collagen as was indicated by light blue/green trichrome staining and positive immunohistochemisty staining for vimentin (FIG. 12C) and prolyl 4-hydroxylase (FIG. 12D). Additionally, numerous blood vessels with red blood cells were found to be present within the hydrogels, Surprisingly, immunohistochemisty staining for $CD8^+$ T-cells (FIG. 12A) indicated a significant number of these cells infiltrating the hydrogel with an average number of 16-30 T-cells per high powered field (400× total magnification). Qualitative evaluation of sections stained for $CD68^+$ macrophages (FIG. 12B) and vimentin (an indicator of fibroblasts) (FIG. 12C) illustrated roughly equal quantities of these cell types present within the hydrogels. Average capsule thicknesses surrounding the explants was 192±67.97 μm and an overall biocompatibility score of 33 was obtained using a modified grading scale. Overall, this would suggest a slight to moderate host reaction to the implant material at the 4 week time-point. (* Indicates implant interstice.)

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of any appended claims and any equivalents thereto.

What is claimed is:

1. A method for forming a hydrogel biomaterial comprising:
   combining collagen, soluble elastin, and at least one glycosaminoglycan to form a mixture;
   heating the mixture to form a gel;
   crosslinking the gel with a first crosslinking agent, the first crosslinking agent forming crosslinks between the collagen and the at least one glycosaminoglycan;
   crosslinking the gel with a second crosslinking agent, the second crosslinking agent stabilizing the soluble elastin; and
   degrading only a portion of the gel following crosslinking with the first and second crosslinking agents with one or more enzymes that target the at least one glycosaminoglycan to form the hydrogel biomaterial, the formed hydrogel, biomaterial exhibiting an equilibrium modulus of from about 3 kilopascals to about 10 kilopascals.

2. The method of claim 1, wherein the mixture is formed at a temperature of less than about 20° C.

3. The method of claim 1, wherein the mixture is heated to a temperature of from about 30° C. to about 40° C. to form the gel.

4. The method of claim 1, wherein the first crosslinking agent is ethyl-3-(-3-dimethylaminopropyl) carbodiimide hydrochloride.

5. The method of claim 1, wherein the first crosslinking agent is provided in conjunction with N-hydroxysuccinimide or a water-soluble analog thereof.

6. The method of claim 5, wherein the N-hydroxysuccinimide is provided in a concentration of about 6 mM or greater.

7. The method of claim 1, wherein the first crosslinking agent is provided in a concentration of about 30 mM or greater.

8. The method of claim 1, wherein the second crosslinking agent is a phenolic compound comprising a hydrophobic core and a plurality of phenol groups extending from the hydrophobic core.

9. The method of claim 1, wherein the second crosslinking agent is pentagalloylglucose.

10. The method of claim 1, wherein the one or more enzymes are provided at a total enzymatic concentration of less than about 10 U/ml.

* * * * *